United States Patent [19]

Legrand et al.

[11] 4,248,884
[45] Feb. 3, 1981

[54] 2-PYRROLIDINE METHANOL DERIVATIVES UTILIZABLE AS MEDICAMENTS

[75] Inventors: Jean-Jacques Legrand, Paris; Christain L. A. Renault, Epinay sur Seine, both of France

[73] Assignee: Pharmindustrie, Gennevilliers, France

[21] Appl. No.: 74,470

[22] Filed: Sep. 11, 1979

[30] Foreign Application Priority Data

Sep. 22, 1978 [FR] France ............................ 78 27178

[51] Int. Cl.³ .................... C07D 207/08; A61K 31/40
[52] U.S. Cl. ............................ 424/274; 260/326.5 R; 260/326.5 FL
[58] Field of Search ............... 260/326.5 R, 326.5 FL; 424/274

[56] References Cited

U.S. PATENT DOCUMENTS

| | | | |
|---|---|---|---|
| 3,006,925 | 10/1961 | Feldkamp et al. | 260/326.5 R |
| 3,077,477 | 2/1963 | Bortnick | 260/326.5 FL |
| 3,732,247 | 5/1973 | Helsley et al. | 260/326.5 R |
| 4,000,160 | 12/1976 | Baily | 260/326.5 R |
| 4,198,424 | 4/1980 | Eestetter et al. | 260/326.5 R |

OTHER PUBLICATIONS

Wagner et al.; Synthetic Organic Chemistry, p. 666 (1965).
Lunsford et al.; Chem. Abs. vol. 70: 87557d (1969).
Helsley et al.; Chem. Abs. vol. 69: 43720b (1968).
Likhosherstou et al.; Chem. Abs. vol. 67, No. 18, 1967, p. 8527, 90642w.

*Primary Examiner*—Mary C. Lee
*Attorney, Agent, or Firm*—Beveridge, DeGrandi, Kline & Lunsford

[57] ABSTRACT

The compounds of the formula:

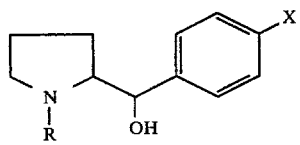

in which X is a hydrogen or halogen atom or an alkoxy group having 1 to 4 carbon atoms, an alkyl or cycloalkyl group having 1 to 8 carbon atoms, and R represents a hydrogen atom, alkyl group having 1 to 4 carbon atoms, or an aralkyl or hydroxyalkyl group in which the alkyl chain has 1 to 4 carbon atoms are disclosed together with processes for their preparation and medicaments containing the compounds. These compounds are hypolipemiants. In addition, some of them are psychostimulants.

7 Claims, No Drawings

2-PYRROLIDINE METHANOL DERIVATIVES UTILIZABLE AS MEDICAMENTS

The present invention relates to new derivatives of 2-pyrrolidine methanol, especially useful as hypolipemiants and more particularly as hypotriglyceridemiants. Some of these derivatives may also be used as psychotropes, more particularly as psychostimulants.

The compounds according to the invention correspond to the following general formula:

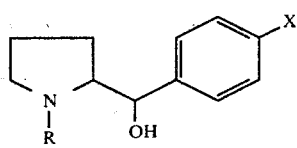

(I)

in which X represents a hydrogen atom, a halogen atom, especially chlorine, bromine, iodine or fluorine, an alkoxy group containing from 1 to 4 carbon atoms, an alkyl or cyclo-alkyl group containing from 1 to 8 carbon atoms and R represents a hydrogen atom, an alkyl group containing from 1 to 4 carbon atoms, or an aralkyl (especially phenylalkyl) or hydroxyalkyl group in which the alkyl chain contains from 1 to 4 carbon atoms.

For a particular definition of the substituents R and X, there are two diastereoisomeric compounds, a threo and an erythro corresponding to the planar formula (I).

The compounds of formula (I) for which R is other than a hydrogen atom may be prepared by alkylation on the nitrogen atom of the compounds corresponding to formula (I) for which R=H. Such an alkylation reaction is effected by means of a suitable alkylating agent, according to known alkylation methods for the alkylation on the nitrogen of secondary amines, for example those described in Wagner and Zook, Synthetic Organic Chemistry, p. 666 (Edition J. Wiley 1965), the disclosure of which is incorporated herein by reference.

The products of formula (I) for which R=H may be prepared by reduction of the products of formula (II):

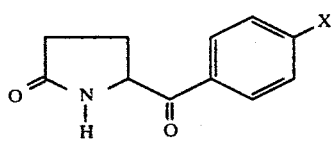

(II)

in which X has the same significance as in the formula (I).

The reducing agent used may be a boron derivative such as diborane or a suitable metal hydride such as lithium aluminium hydride, preferably in excess. The operation is effected in an inert solvent such as ether or tetrahydrofuran, at a temperature between 20° C. and the boiling temperature of the solvent used. Once the reduction is completed, the reaction mixture is treated with water in the presence of sodium hydroxide and at low temperature such as from −5° to +5° C., the mineral precipitate formed is separated by filtration and the filtrate is evaporated.

The processes described above generally lead to a mixture of the two isomers threo and erythro, which isomers may be separated by conventional methods, e.g. physical (crystallization, chromatography, etc.) or chemical (formation of the salt and regeneration of the base, etc.). The preponderant isomer is generally isolated easily from the crude product of the reaction by a simple recrystallization.

An advantageous method for obtaining the other isomer consists in isomerizing the preponderant isomer by the successive action of an acid chloride, such as thionyl chloride, and water, according to the methods known per se, such as that described in the Journal of Organic Chemistry, 1968, 33, 1762, the disclosure of which is incorporated herein by reference.

The compounds of formula (I) in the form of free bases can if desired be converted into salts of addition with a mineral or organic acid by the action of such an acid in a suitable solvent. Suitable such acids include organic acids such as acetic, propionic, tartaric, citric, methanesulfonic or inorganic acids such as hydrochloric, hydrochromic, sulphonic.

The compounds of formula (II), which are new products, can be prepared by the reaction of pyroglutamic acid chloride of formula (III) with a benzene derivative of formula (IV), in which X has the same significance as in formula (I), according to the equation:

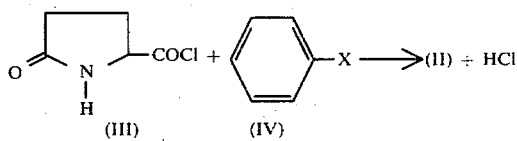

This reaction is effected in the presence of a catalyst taken from those known as Friedel Crafts catalysts (metallic halides, metal oxides, iodine, mineral acids) under conditions such as those described by Wagner and Zook, Synthetic Organic Chemistry, p. 317, (Edition J. Wiley—1965), the disclosure of which is incorporated herein by reference. An advantageous method consists in operating with aluminium chloride as catalyst, in the absence or presence of a solvent. Examples of suitable solvents which may be used are carbon tetrachloride and carbon disulfide.

The acid chloride of formula (III) is a known product (cf. W. Voss, Z. Physiol. Chem., 1932, 204, 1). It may be prepared from pyroglutamic acid by a process analogous to that described in J. Prakt. Chem., 1957, 5. pp. 91–96, the disclosure of which is incorporated herein by reference.

The pathogenic part of the very low density lipoproteins (or V.L.D.L.) in the formation and evolution of the dislipemia (i.e. the disorders of the metabolism of the lipids expressed by an abnormally high proportion of fats circulating in the blood) justifies the therapeutic interest of products capable of retarding the production of these lipoproteins. Given the richness in triglycerides of these light lipoproteins, it seems that one of the best ways for reducing their proportion in plasma is to reduce the proportion of the circulating triglycerides.

The compounds of formula (I) possess the property of being able to reduce the amount of circulating triglycerides. In addition, some of these compounds belonging to the erythro series have a remarkable action on the central nervous system, especially a psychostimulant action.

The following examples illustrate the invention without it being limited thereto. The results of the analyses by nuclear magnetic resonance (N.M.R.) given in these examples have been obtained by dissolving the products

EXAMPLE 1

α-phenyl-2-pyrrolidine-methanol (erythro isomer)

(a) Preparation of 5-benzoyl-2-pyrrolidone.

300 g of phosphorus pentachloride are added at −10° C. in a period of 20 minutes to a suspension of 142 g of pyroglutamic acid in 930 ml of acetyl chloride. The temperature is maintained at 0° C. for 4 hours. The rose-colored precipitate formed is separated and washed twice with 100 ml of benzene each time.

The acid chloride thus obtained (pyroglutamic acid chloride) is suspended in 3 liters of anhydrous benzene. The 300 g of aluminium chloride are added in small fractions, and the mixture is then heated for 12 hours under reflux. It is cooled to the ambient temperature and the reaction mixture is then poured on to a mixture of 3 kg of ice and 300 ml of concentrated hydrochloric acid. This is stirred for 2 hours at the ambient temperature and then the beige precipitate obtained is separated. The latter is suspended in 150 ml of ethyl acetate, then drained and dried under vacuum. 121.5 g of 5-benzoyl-2-pyrrolidone melting at 175° C. are thus obtained.

(b) Preparation of α-phenyl-2-pyrrolidine methanol (erythro isomer)

65.6 g of 5-benzoyl-2-pyrrolidone prepared as indicated in above part (a) are added in small fractions, under a nitrogen atmosphere, to a suspension of 26.4 g of lithium aluminium hydride in 4 liters of anhydrous tetrahydrofuran. The mixture is then refluxed with stirring for 2 hours. It is then cooled to 0° C. and then are slowly added 30.5 ml of water, then 11 ml of a 10 N solution of sodium hydroxide and finally 110 ml of water. After having stirred for 2 hours at the ambient temperature, the precipitate formed is separated by filtration. The filtrate obtained is dried over magnesium sulfate and the solvent is distilled under reduced pressure. 53 g of α-phenyl-2-pyrrolidine methanol are obtained. These 53 g are recrystallized from 580 ml of isopropyl ether. 36 g of α-phenyl-2-pyrrolidine methanol (erythro) melting at 110° C. are thus obtained.

Elementary analysis of the product obtained:

|  | C % | H % | N % |
| --- | --- | --- | --- |
| Found: | 62.05 | 7.6 | 6.38 |
| Calculated: | 61.9 | 7.5 | 6.55 |

EXAMPLE 2

Preparation of α-phenyl-2-pyrrolidine methanol (threo isomer)

100 ml of thionyl chloride are added drop by drop to a solution of 52.4 g of α-phenyl-2-pyrrolidine methanol (erythro isomer) in 500 ml of chloroform, cooled to 0° C. The mixture is stirred for 1 hour at the ambient temperature. The solution is then run on 1.5 kg of ice and the mixture is stirred for 30 minutes, then decanted. The aqueous phase is then heated under reflux for 2 hours, then cooled to 0° C. and brought to pH 11 with sodium hydroxide. The oil which salted out is extracted 4 times with 200 ml of chloroform each time. The organic phase is dried over magnesium sulfate and the solvent is evaporated under vacuum. The 50.6 g of oil obtained are dissolved in 300 ml of anhydrous ethyl ether. 60 ml of a 5 N solution of hydrochloric acid in ether are added drop by drop. The mixture is cooled to 0° C. and stirred for 15 minutes. The white precipitate obtained is separated, washed 3 times with 50 ml of anhydrous ethyl ether each time and dried under vacuum. 60 g of crude α-phenyl-2-pyrrolidine methanol hydrochloride (threo) melting at 160° C. are thus obtained.

These 60 g are recrystallized from 250 ml of isopropanol. 52 g of α-phenyl-2-pyrrolidine methanol hydrochloride (threo) melting at 176° C. are thus obtained.

Elementary analysis of the product obtained:

|  | C % | H % | N % |
| --- | --- | --- | --- |
| Found: | 61.81 | 7.62 | 6.39 |
| Calculated: | 61.9 | 7.5 | 6.55 |

EXAMPLE 3

Preparation of α-phenyl-2-(1-benzyl-pyrrolidine) methanol (threo isomer)

A suspension of 11.7 g of α-phenyl-2-pyrrolidine methanol (threo), 11.3 g of benzyl bromide and 10.8 g of sodium acetate in 170 ml of absolute ethanol is heated for 1 hour under reflux. It is then cooled to the ambient temperature, and the solvent is distilled off under reduced pressure. The pasty mass obtained is taken up in 100 ml of water. The oil which separates is extracted twice with 100 ml of chloroform each time. After drying the organic phase over magnesium sulfate the solvent is removed by distillation under reduced pressure. 17.6 g of yellow oil are obtained which are dissolved in 100 ml of petrol ether. After standing over night at 0° C., the precipitate formed is separated. 14.5 g of α-phenyl-2-(1-benzyl-pyrrolidine)methanol (threo) melting at 190° C. are thus obtained.

N.M.R. spectrum of the product obtained: Proton in α position with respect to OH: chemical displacement δ=4.4 ppm.

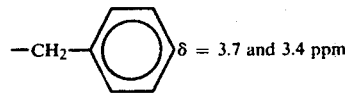

EXAMPLE 4

Preparation of α-phenyl-2-(1-methyl-pyrrolidine)methanol (threo isomer)

A mixture of 8.9 g of α-phenyl-2-pyrrolidine methanol (threo), 1.7 ml of 99% formic acid, 5.4 g of formol at 30% by volume and 55 ml of water is heated at 140° C. in an autoclave. After heating over night at 140° C., the mixture is cooled to the ambient temperature, made alkaline by addition of a 38% aqueous solution of sodium hydroxide, and potassium carbonate is added to the aqueous solution up to saturation. The oil which is salted out is extracted three times with 100 ml each time of chloroform. The organic phase is dried over magnesium sulfate. The solvent is distilled off under reduced pressure, and 9.5 g of a light brown oil are obtained. The oil is solubilized in 100 ml of acetone and 5.7 g of fumaric acid dissolved in 30 ml of acetone are added. The fumarate obtained is separated by filtration. 9.5 g of the fumarate of α-phenyl-2-(1-methyl-pyrrolidine)methanol (threo) which melts at 156° C. are thus obtained.

N.M.R. spectrum of the product obtained: Proton in α position with respect to OH: δ=4.4 ppm —CH₃: δ=2.2 ppm.

EXAMPLE 5

Preparation of α-phenyl-2-(1-β-hydroxyethyl-pyrrolidine)methanol (threo isomer)

A benzene solution of 4.8 g of α-phenyl-2-pyrrolidine methanol (threo) to which has been added 5 ml of triethylamine and 3.4 g of 2-bromo-ethanol is heated under reflux over night. It is cooled to the ambient temperature, the precipitate of triethylamine hydrobromide formed is separated and the solvent is distilled off under reduced pressure. 3.8 g of an orange oil are obtained which crystallizes by addition of 7.6 ml of isopropyl ether. 3 g of α-phenyl-2-(1-β-hydroxyethyl-pyrrolidine)methanol (threo), which melts at 68° C., are thus obtained.

N.M.R. spectrum of the product obtained: Proton in α position with respect to the OH: δ=4.3 ppm —CH₂OH: δ=3.6 ppm.

EXAMPLE 6

α-(4-chloro-phenyl)-2-pyrrolidine methanol (erythro isomer)

(a) Preparation of 5-(4-chloro-benzoyl)-2-pyrrolidone

The operation is as in part (a) of Example 1 but the 142 g of pyroglutamic acid are replaced by 35 g of this same acid, the 300 g of phosphorus pentachloride are replaced by 75 g of phosphorus pentachloride, and the three liters of anhydrous benzene are replaced by 200 ml of chlorobenzene.

30 g of 5-(4-chloro-benzoyl)-2-pyrrolidone are obtained, which melts at 174° C.

(b) Preparation of α-(4-chloro-phenyl)-2-pyrrolodine methanol (erythro isomer)

The operation is as in part (b) of Example 1 but the 65.6 g of 5-benzoyl-2-pyrrolidone are replaced by 15 g of 5-(4-chloro-benzoyl)-2-pyrrolidone.

8 g of α-(4-chloro-phenyl)-2-pyrrolidine methanol (erythro) are obtained in the form of the hydrochloride melting at 177° C.

Elementary analysis of the product obtained:

|  | C % | H % | N % | Cl % |
| --- | --- | --- | --- | --- |
| Found: | 52.85 | 6.16 | 5.47 | 27.95 |
| Calculated: | 53.2 | 6.05 | 5.65 | 28.6 |

EXAMPLE 7

Preparation of α-(4-chloro-phenyl)-2-pyrrolidine methanol (threo isomer)

The operation is as in Example 2 but the 52.4 g of α-phenyl-2-pyrrolidine methanol (erythro isomer) are replaced by 10 g of α-(4-chloro-phenyl)-2-pyrrolidine methanol (erythro isomer). 8 g of α-(4-chloro-phenyl)-2-pyrrolidine methanol (threo) are obtained in the form of the hydrochloride melting at 190° C.

Elementary analysis of the product obtained:

|  | C % | H % | N % |
| --- | --- | --- | --- |
| Found: | 53.72 | 6.13 | 5.67 |
| Calculated: | 53.23 | 6.05 | 5.63 |

EXAMPLE 8

α-(4-cyclohexyl-phenyl)-2-pyrrolidine methanol (erythro isomer)

(a) Preparation of the 5-(4-cyclohexyl-benzoyl)-2-pyrrolidone.

The operation is as in the first part of Example 1, but the 142 g of pyroglutamic acid, the 300 g of PCl₅ and the three liters of anhydrous benzene are replaced respectively by 20 g of pyroglytamic acid, 43 g of PCl₅ and 25 g of cyclohexyl benzene.

There are obtained 20 g of 5-(4-cyclohexyl-benzoyl)-2-pyrrolidone which melts at 200° C.

(b) Preparation of α-(4-cyclohexyl-phenyl)-2-pyrrolidine methanol (erythro isomer)

The operation is as in part (b) of Example 1 but the 65.6 g of 5-benzoyl-2-pyrrolidone are replaced by 10 g of 5-(4-cyclohexyl-benzoyl)-2-pyrrolidone.

7.2 g of α-(40 cyclohexyl-phenyl)-2-pyrrolidine methanol (erythro) are obtained in the form of the hydrochloride melting at 210° C.

Elementary analysis of the product obtained:

|  | C % | H % | N % |
| --- | --- | --- | --- |
| Found: | 68.77 | 8.87 | 4.59 |
| Calculated: | 69.1 | 8.8 | 4.73 |

EXAMPLE 9

Preparation of α-(4-cyclohexyl-phenyl)-2-pyrrolidine methanol (threo isomer)

The operation is as in Example 2, but 52.4 g of α-phenyl-2-pyrrolidine methanol (erythro) are replaced by 5 g of α-(4-cyclohexyl-phenyl)-2-pyrrolidine methanol (erythro). 4.5 g of α-(4-cyclohexyl-phenyl)-2-pyrrolidine methanol (threo) are obtained, in the form of the oxalate melting at 139° C.

Elementary analysis of the product obtained:

|  | C % | H % | N % |
| --- | --- | --- | --- |
| Found: | 65.37 | 7.88 | 4.00 |
| Calculated: | 65.33 | 7.74 | 4.01 |

EXAMPLE 10

α-(4-tertiobutyl-phenyl)-2-pyrrolidine methanol (erythro isomer)

(a) Preparation of the 5-(4-tertiobutyl-benzoyl)-2-pyrrolidone.

The operation is as in part (a) of Example 1 but the 142 g of pyroglutamic acid, the 300 g of PCl₅ and the 3 liters of anhydrous benzene are replaced respectively by 40 g of pyroglutamic acid, 90 g of PCl₅ and 42 g of tertiobutylbenzene.

30 g of 5-(4-tertiobutyl-benzoyl)-2-pyrrolidone are obtained which melts at 144° C.

(b) Preparation of
α-(4-tertiobutyl-phenyl)-2-pyrrolidine methanol
(erythro isomer)

The operation is as in part (b) of Example 1 but the 65.6 g of 5-benzoyl-2-pyrrolidone are replaced by 15 g of 5-(4-tertiobutyl-benzoyl)-2-pyrrolidone.

10 g of α-(4-tertiobutyl-phenyl)-2-pyrrolidine methanol (erythro) are obtained in the form of the hydrochloride melting at 199° C.

Elementary analysis of the product obtained:

|  | C % | H % | N % |
|---|---|---|---|
| Found: | 66.76 | 8.98 | 5.21 |
| Calculated: | 66.8 | 8.9 | 5.19 |

EXAMPLE 11

Preparation of α-(4-tertiobutyl-phenyl)-2-pyrrolidine methanol (threo isomer)

The operation is as in Example 2, but the 52.4 g of α-phenyl-2-pyrrolidine methanol (erythro) are replaced by 10 g of α-(4-tertiobutyl-phenyl)-2-pyrrolidine methanol (erythro). 8 g of α-(4-tertiobutyl-phenyl)-2-pyrrolidine methanol (threo) are obtained in the form of the hydrochloride, melting at 190° C.

N.M.R. spectrum of the product obtained: Proton in a position with respect to OH: δ=4.3 ppm

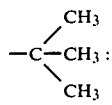

δ=1.4 ppm

PHARMACOLOGICAL PROPERTIES (1) Hypotriglyceridemiant activity

With the object of determining if the compounds of the present invention have the property of reducing an abnormally high proportion of triglycerides, it was attempted to induce an experimental hypertriglyceridemia in an animal. The administration of a determined quantity of oil (olive oil) to the fasting animal has proved in this respect a reliable method, previously used by A. Bizz and others—Europ. Journal of Pharmacology, 1973, 23, 131, the disclosure of which is incorporated herein by reference.

Male rats weighting about 200 g which had fasted for 18 hours are treated orally with the products to be studied, then two hours after, 20 ml/kg of olive oil are orally administered to them. The rats are killed two hours after the administration of the oil by decapitation. The serum is separated by centrifuging and the triglycerides are determined on an amount of 0.2 ml of serum by extraction with a heptane-isopropanol mixture and colorimetry according to the method of Van Handel et al., J. Lab. and Clin. Med., 1957, 50, 152-157, by using an assembly of analytical reagents known commercially as "Triclycerides-kit Bio Merieux".

The proportions of triglycerides obtained, expressed in mg of triglycerides (calculated as triolein) per ml of serum, are compared with the proportions of triglycerides of the control animals (animals not treated with the products and to which 20 ml/kg per os of olive oil has been administered), and the results are expressed in a percentage of inhibition, which represents the relative percentage reduction of the proportion of triclycerides in the treated animals with respect to this same proportion in the control animals.

The results are collected in the following Table 1 in which is also given by way of comparison the result provided by nicotinic acid, the reference product.

TABLE 1

| Products | Doses (mg/kg) | Method of administration | % of inhibition | Statistic meaning of the results according to the T test of Student Fischer |
|---|---|---|---|---|
| Nictotinic acid | 100 | oral | 50 | 0.01 |
| Example 1 | 50 | oral | 33 | 0.05 |
| Example 2 | 50 | oral | 45 | 0.01 |
|  | 6.25 | oral | 41 | 0.01 |
| Example 5 | 100 | oral | 45 | 0.01 |
| Example 7 | 100 | oral | 41 | 0.01 |

As seen in Table 1, the products according to the invention are remarkable hypotriglyceridemiants.

In particular, the product of Example 2 is still very active at the dose of 6.25 mg/kg by oral administration.

(2) Action on the central nervous system

The activity of the products on the central nervous system has been shown by the test of reserpine induced hypothermia in mice, according to the method of D. M. Asken, Life Sciences, 1963, vol. 2, p. 725, the disclosure of which is incorporated herein by reference, The results are expressed by a $DE_{50}$ or dose of product, in mg/kg, capable of exerting an antihypothermic effect equal to 50% of the antihypothermic effect caused by 15 mg/kg (oral) of imipramine.

The results obtained are collected in the following Table 2:

TABLE 2

| Product of Example | $DE_{50}$ oral (mg/kg) |
|---|---|
| 1 | 4.5 |
| 2 | >150 |
| 6 | 18 |
| 7 | > 50 |

Table 2 shows the difference of activity on the central nervous system existing between the stereoisomers corresponding to an identical developed formula. Whereas the products of the threo series have a very feeble activity on the central nervous system, certain products of the erythro series have a notable psychostimulant action.

This difference in activity on the central nervous system enables certain compounds of formula (I) to be used as psychotropes and others as hypolipemiants without action on the central nervous system.

TOXICOLOGICAL PROPERTIES

The acute toxicities of the compounds according to the invention have been determined on the male mouse $CD_1$ (Charles River) by oral administration. The $LD_{50}$ have been calculated, after three days of observation, by the cumulative method of J. J. Reed et al. (Am. J. Hyg., 1938, 27, 493), the disclosure of which is incorporated herein by reference.

The $LD_{50}$ obtained are collected in the following Table 3:

TABLE 3

| Products of Example | LD$_{50}$ oral (mg/kg) |
| --- | --- |
| 2 | 600 |
| 5 | 675 |
| 7 | 400 |
| 10 | 600 |
| 3 | 270 |
| 4 | 800 |
| 6 | 675 |
| 8 | >900 |

The compounds of formula (I) therefore act as substances of relatively little toxicity to mice.

THERAPEUTIC USE

The compounds of formula (I) and their salts with pharmaceutically acceptable acids may be used in human therapeutics in the form of compressed tablets, capsules, gelatine-coated pills, suppositories, ingestable or injectable solutions, etc., for the treatment of the dislipemias. Some are also utilizable as psychotropes, more particularly as psychostimulants.

The posology depends on the effects required and on the method of administration used. For example, taken orally, it may comprise between 50 and 500 mg of active substance per day, with single doses going from 10 to 100 mg.

What is claimed is:

1. The compound of the formula:

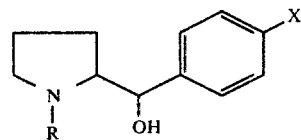

in which X is hydrogen, a halogen atoms, an alkoxy group containing 1 to 4 carbon atoms, an alkyl group or cycloalkyl group containing 1 to 8 carbon atoms, and R represents hydrogen, an alkyl group containing 1 to 4 carbon atoms, or a phenylalkyl or hydroxyalkyl group in which the alkyl chain contains 1 to 4 carbon atoms.

2. The compound according to claim 1 which is α-phenyl-2-pyrrolidine methanol (threo isomer).

3. The compound according to claim 1 which is α-phenyl-2-(1-benzyl pyrrolidine)methanol (threo isomer).

4. The compounds of the formula:

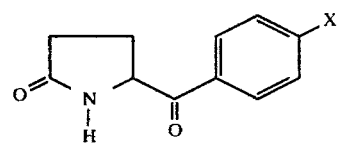

in which X has the same definition as in claim 1.

5. A medicament, useful as a hypolipemiant or psychotrope, which contains as active ingredient a compound according to claim 1 or a salt of said compound with a pharmaceutically acceptable acid.

6. A medicament according to claim 5 in which the active agent compound is α-phenyl-2-pyrrolidine methanol (threo isomer) or a salt of this compound with a pharmaceutically acceptable acid.

7. A medicament according to claim 5 in which the active agent is α-phenyl-2-(1-benzyl-pyrrolidine)methanol (threo isomer) or a salt of this compound with a pharmaceutically acceptable acid.

* * * * *